United States Patent [19]

Baker et al.

[11] Patent Number: 4,850,716
[45] Date of Patent: Jul. 25, 1989

[54] REMOTELY DETECTABLE STERILIZATION MONITOR

[75] Inventors: Dennis L. Baker, St. Joseph Township, St. Croix County, Wis.; Steven S. Kirckof, Oakdale, Minn.; Dan J. Morse, Minneapolis, Minn.; Chester Piotrowski, White Bear Lake, Minn.

[73] Assignee: Minnesota Mining and Manufacturing Company, Saint Paul, Minn.

[21] Appl. No.: 123,198

[22] Filed: Nov. 20, 1987

[51] Int. Cl.⁴ .................. G01K 1/08; G01K 11/06
[52] U.S. Cl. .................................. 374/160; 116/204; 116/217; 335/215; 340/590; 374/177
[58] Field of Search .................. 374/160, 176, 177; 116/217, 207; 335/215

[56] References Cited

U.S. PATENT DOCUMENTS

| Re. 32,428 | 5/1987 | Gregor et al. | 340/572 |
|---|---|---|---|
| 1,191,572 | 7/1916 | Davis | 374/160 X |
| 3,174,716 | 3/1965 | Salter | 335/215 X |
| 3,209,181 | 9/1965 | Brockman et al. | 335/215 X |
| 3,554,001 | 1/1971 | Norem | 374/1 |
| 3,675,501 | 7/1972 | De Kanter | 116/217 X |
| 3,684,737 | 8/1972 | Emigh | 252/408 |
| 3,696,679 | 10/1972 | Peterson et al. | 374/160 X |
| 3,981,683 | 9/1976 | Larsson et al. | 116/207 X |
| 4,092,625 | 5/1978 | Newson | 116/217 |
| 4,187,799 | 2/1980 | Zwarun | 116/217 |
| 4,448,548 | 5/1984 | Foley | 374/160 |
| 4,591,566 | 5/1986 | Smith | 435/291 |
| 4,664,310 | 2/1987 | Anderson, III et al. | 335/215 |

Primary Examiner—Daniel M. Yasich
Attorney, Agent, or Firm—Donald M. Sell; Walter N. Kirn; Peter Forrest

[57] ABSTRACT

A monitor for detection of temperature and/or steam conditions indicative of sterilization. The monitor comprises means for creating a remotely detectable response upon interrogation by an electromagnetic field and means for changing the response upon exposure to a predetermined set of temperature and steam conditions. The remotely detectable response is preferably produced through the interaction of an electromagnetic interrogation field with magnetic components of the monitor, wherein the characteristic harmonic response generated by the magnetic components is either inhibited or enabled by the change in configuration of one or more elements of the detector. Sterilization conditions are detected through one or more compounds known to have melting points which are above the temperature used in the sterilization process. Melting of the chemical compound produces the change in configuration of the element or elements of the monitor.

15 Claims, 2 Drawing Sheets

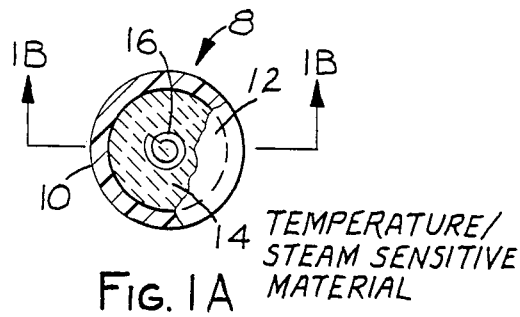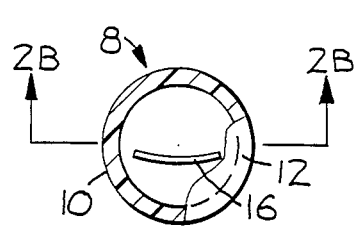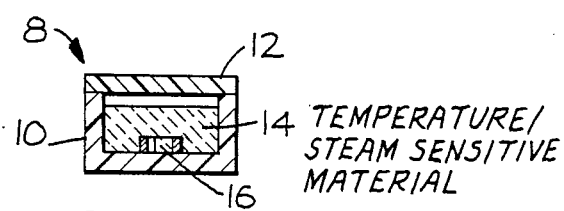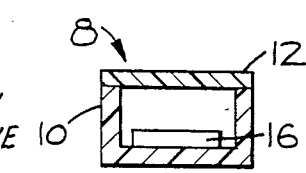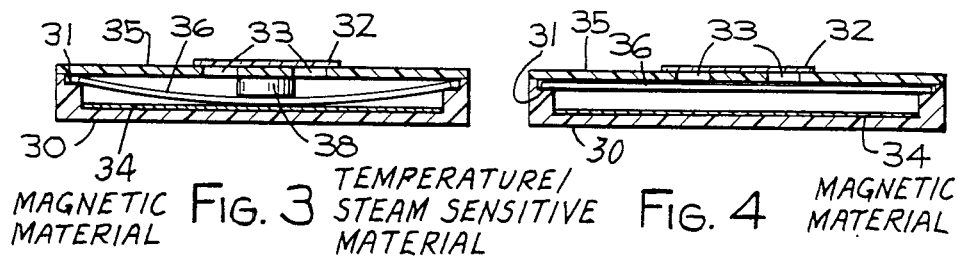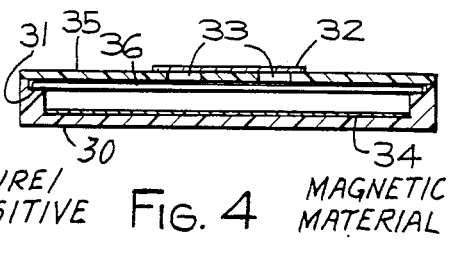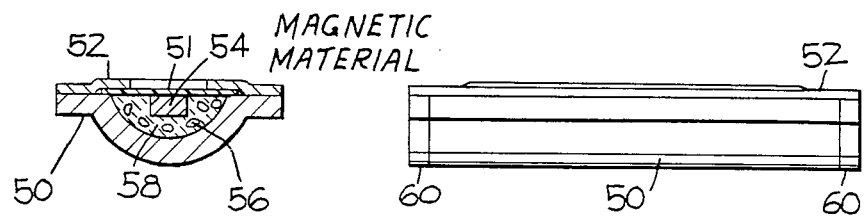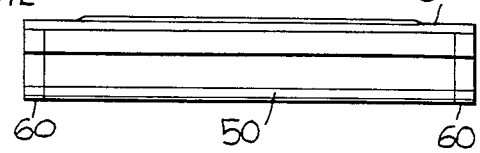

REMOTELY DETECTABLE STERILIZATION MONITOR

TECHNICAL FIELD

This invention relates to a sterilization monitor wherein a change in electromagnetic characteristics of the monitor caused upon exposure to sterilization conditions is remotely detectable within an interrogation zone.

BACKGROUND

Many items used in surgical suites are sterilized in advance of use and stored until needed. Bowls, pans, and the like are generally wrapped in two layers of cloth and sterilized in an autoclave, a device for generating saturated steam at high temperature, typically 250° F. to 273° F. (121° C. to 134° C.). Proper management of the sterile field in the suite requires verification of the sterility of the items before use. One present practice is to attach to the outside of the pack a steam sterilization monitor which indicates if temperature, humidity, and time conditions indicative of sterilization have occurred. One limitation of present monitors is that they cannot remotely detect whether the desired temperature and humidity conditions necessary for proper sterilization were present inside the cloth layers at the surface of the bowl or pan.

One present type of monitor, such as set forth in U.S. Pat No. 4,448,548, displays a change in color, or the wicking of a substance, or both, and thus requires a visual inspection. Similarly, monitors containing microorganisms, such as depicted in U.S. Pat. No. 4,591,566, require culturing the spores exposed to the sterilization process and cannot be remotely inspected. Monitors of these types are therefore less suitable for placement within the layers of cloth wrapped around the bowl or pan, as they cannot be inspected without removing the cloth layers. To prevent compromising the sterility of the contents, this inspection would have to be done immediately before use of the sterilized item in the suite. However, should the monitor show that the pack contents are not sterile, the surgical sterile field may be compromised, or at best, the surgical procedure is delayed while a replacement pack is obtained, if one is available. Therefore, a sterilization monitor which could be inspected without removing the sterile cloth would improve the management of surgical sterile fields as well as that of the inventory of the sterile items used in surgical suites.

A well-established technology to monitor the presence of objects in a given zone is employed in electromagnetic surveillance systems, such as that depicted in U.S. Pat. Re. No. 32,428. Typically, as set forth in that patent, a "marker" having certain magnetic properties so as to be capable of providing characteristic response when interrogated by an alternating magnetic field, is attached to the object to be monitored. When the marker passes through such an applied magnetic field in an "interrogation zone," the characteristic electromagnetic response is created and detected by appropriate circuitry. For applications in which a marker is to be permanently attached to an object, as in the spine of a book, and is desired to be deactivated, e.g., when the book has been properly checked out of a library, the surveillance system further comprises means for changing the response when desired.

DISCLOSURE OF INVENTION

The invention is a remote temperature monitor comprising means for creating a remotely detectable response upon interrogation by a low intensity magnetic field, and means for changing the creating means, and hence the response upon exposure to a predetermined temperature.

Conditions indicative of sterilization are preferably detected through the melting of inexpensive and readily-available compounds. When the sterilization process to be monitored employs steam in addition to elevated temperatures, the compound is selected to have a melting point which is decreased by steam into the temperature range employed in the process. For example, autoclaves operate on the principle that the destruction of bacterial spores is most efficient when both elevated temperatures and steam are present. Thus, the melting of a compound which is sensitive to both temperature and steam indicates if both conditions are met. Proper packaging of the compound, such as in a mixture of polymeric binders or within polypropylene or nylon films, slows the melting to a period of time typical of sterilizer operating cycles. This delay can also be achieved by adding suitable materials to the temperature and/or steam sensitive compound, employing a binding agent if required.

In the monitor of the present invention, the means for creating a remotely detectable magnetic response comprises a ferromagnetic material of high permeability and low coercivity. This means has at least two distinct magnetic states or configurations, is changed from the first to the second state or configuration by the changing means, and responds to a low intensity, alternating magnetic field in a manner unlike that of commonly occurring ferrous objects. It is thus known to use high permeability, low coercive force materials having shapes selected such that internal demagnetization effects are controlled. When the magnetization of such shaped materials is rapidly reversed by an applied alternating field, readily detectable, high order harmonics of the applied field frequency are produced. The harmonic content, and hence characteristic response produced upon magnetization reversal, may be changed, for example, by placing strain in the material, changing its shape (and therefore, its demagnetization factor) or by magnetically biasing the material.

Thus, in the present invention, the means for changing the creating means, and hence the remotely detectable magnetic response, comprises a material which melts upon being heated to a predetermined temperature, and which upon so melting is preferably used to create or allow a change in the shape of a magnetic material (which in turn effects a change in the magnetic characteristics of the monitor), or to create or allow a change in the position of the material relative to a magnetic bias field to similarly effect a change in the remotely detectable magnetic response. The change in state or configuration and hence in magnetic state can then be remotely detected using interrogation and sensing techniques such as those used in electromagnetic article surveillance systems. In the first state, a first remotely detectable magnetic response is created upon a first interrogation, and in the second state, a second remotely detectable magnetic response, different from the first, is created upon a second interrogation.

BRIEF DESCRIPTION OF DRAWING

FIG. 1A is a top view of one embodiment of the invention, shown before exposure to sterilization conditions, with part thereof broken away and shown in section.

FIG. 1B is a side view of the monitor of FIG. 1A, taken along the line 1B—1B of FIG. 1A.

FIG. 2A is a top view of the monitor of FIG. 1A, shown after exposure to sterilization conditions, with part thereof broken away and shown in section.

FIG. 2B is a side view of the monitor of FIG. 2A, taken along the line 2B—2B of FIG. 2A.

FIG. 3 is a section view of a second embodiment of the invention, shown before exposure to sterilization conditions.

FIG. 4 is a section view of the monitor of FIG. 3, shown after exposure to sterilization conditions.

FIG. 5 is a section view of a third embodiment of the invention.

FIG. 6 is a side view of the monitor of FIG. 5.

DETAILED DESCRIPTION

Figure 7:
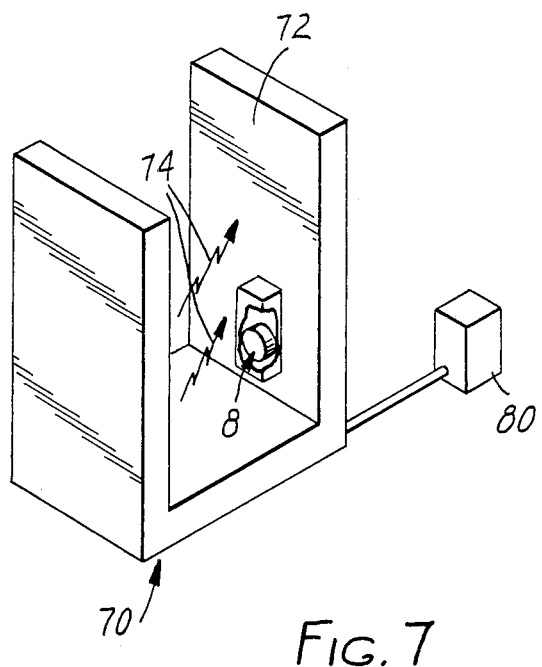
FIG. 7 is a schematic view of a detection system suitable for use with this invention.

A preferred embodiment of the invention, suitable for a sterilization process employing steam, is shown in FIGS. 1A and 1B. As there shown, the monitor 8 comprises a housing 10, which must be comprised of a material which will withstand the elevated temperatures, humidity levels, and other conditions present in sterilization equipment such as autoclaves. In the preferred embodiment, the housing 10 is comprised of 0.030 inch (0.76 millimeter) thick polypropylene, assembled by means known in the art of producing an assembly which will withstand the same conditions as the housing. Such means include heat setting and the use of known adhesives. The housing is shaped as a right circular cylinder with one end closed.

A circular "steam window" 12, suitably attached to the housing, and closing the other end of the cylinder, comprises a material which will readily pass the saturated steam into the inside of the monitor. Preferably this is a 0.002 inch (0.05 mm) thick film of polypropylene, with the cylinder) chosen to allow sufficient quantities of steam to reach the inside of the housing 10. Within the housing are positioned a temperature/steam sensitive material 14 and a magnetic material 16, with movement or change in the shape of the magnetic material being restricted by virtue of being encased within the temperature/steam sensitive material 14. The magnetic material 16 is coiled into a first, compact configuration having a spiral-like shape having a relatively high demagnetization factor such that it exhibits a first response, i.e., that only low order harmonics of the applied field frequency are produced upon interrogation by an applied external magnetic field having an intensity in the low range typical of electromagnetic article surveillance systems. FIG. 7 shows schematically a suitable detection system 70, which comprises a low intensity magnetic field 74 produced within an interrogation zone 72 and detected by field creation and detection apparatus 76. A preferred magnetic material also possesses a sufficient spring constant to cause it to uncoil when the temperature/steam sensitive material melts and no longer constrains the ferromagnetic material 16 in the coiled configuration. Upon uncoiling, the material 16 assumes a second configuration having a much lower demagnetization factor and thus, upon such interrogation, exhibits a second response, i.e., that at which a detectable, high-harmonic content, response is produced.

In the preferred embodiment of FIGS. 1A and 1B, the ferromagnetic material may be any of a variety of compositions known in the art to generate a detectable response, and which are substantially immune to work hardening. It is known in the art that many ferromagnetic materials otherwise suitable for use with article surveillance systems, upon bending, exhibit a loss of ability to respond to interrogation. Such materials are not preferred for this embodiment because the coiling and uncoiling required may result in sufficient work hardening to prevent response when the material is uncoiled. Amorphous metallic alloys are commonly employed in the art, as they have been found to have the desired immunity to work hardening. The alloy may have many different combinations of metal constituents.

The preferred magnetic material 16 for this embodiment was a strip of amorphous foil, composed of cobalt (68.5 atomic percent) boron (12.4%), silicon (10%), iron (4.2%), nickel (3.4%), and molybdenum (1.5%). This material is available from Allied-Signal Corporation as type 2705M. The strip of amorphous foil was 2.625 inches (6.7 centimeters) long, 0.06 inch (0.15 centimeter) wide, and 0.0008 (0.020 millimeter) inch thick. It was coiled into a diameter of approximately 0.25 inch (6.35 millimeters).

The temperature/steam sensitive material may be any of the known compositions having the property that their melting points are depressed in the presence of saturated steam into the temperature range typical of the sterilizing equipment, but normally are higher than such temperatures. Thus, the melting of the material indicates the presence of steam at a minimum temperature. As taught by U.S. Pat. No. 3,981,683, such materials include 2-chloroacetamide, 2-ethoxybenzamide, benzoic acid, diphenyl succinate, dichlorophenol, dimethyl phenol, benzamide, urea, 1,4 dihydroxybenzophenone, hydroquinone, dioxime, ethylene ester of toluene sulfonic acid, salicylamide, and salicylic acid. Another suitable compound is sebacic acid (1,8-octane dicarboxylic acid). The preferred material for the present invention is salicylamide.

The melting time of the material can be controlled in the manner taught by U.S. Pat. No. 4,448,548. A binder is added to the material to allow it to be shaped into tablet form, with the added benefit of delaying the melting time of the entire tablet as the percentage of binder increases. Polyvinylpyrrolidone (PVP) is a preferred additive. The tablet may contain other materials desirable for mass production efficiency or other reasons.

In the embodiment of FIGS. 1A and 1B 80% salicylamide and 20% polyvinylpyrrolidone mixture is a preferred combination. A preferred size is a right circular cylinder approximately 0.25 inch (6.35 millimeters) in height and 3 inches (7.62 centimeters) in diameter.

Upon exposure of the monitor to sterilization conditions, as in an autoclave, the saturated steam passes through the steam window 12, melts the temperature/steam sensitive material 14, and thereby permanently changes the response of the monitor, as the melting allows the magnetic material 16 to uncoil, as shown in FIGS. 2A and 2B. The temperature/steam sensitive material will re-solidify once sterilization conditions cease, but is not shown in FIGS. 2A and 2B for clarity. The magnetic material has now uncoiled to a configuration in which it will suitably generate the high order harmonics of the frequency of the applied magnetic field which can be sensed by the detection apparatus, thereby enabling a remote indication that sterilization conditions have occurred.

As shown in FIG. 7, the field creation and detection apparatus 76 may be any means known in the art for generating an applied magnetic field and detecting a response from the magnetic material of the monitor within an interrogation zone 72. Such systems generally emit a periodically alternating magnetic field of a known frequency and are tuned to respond to electromagnetic signals within a limited range of harmonics of that frequency. The composition and shape of the magnetic material are selected such that the magnetization of the magnetic material is readily reversed by such applied fields. Suitable materials typically exhibit high permeability and low coercivity. Thus, when "interrogated" by the applied field, the magnetization of the magnetic material reverses at each alternation of the applied field. Each such reversal produces harmonics of the applied field frequency which may be detected to indicate the presence of the magnetic material within the interrogation zone. The applied field strength and frequency are chosen as required for the application. Lower applied frequencies are desirably used if the harmonics generated are likely shielded from the detection means by objects (usually metallic) in the interrogation zone. The detection means may be a free-standing unit or hand-held as required by the application.

In addition to the above noted advantage regarding the immunity to work hardening, amorphous ferromagnetic materials are known to provide higher amplitude response to applied fields, and so are further preferred because this allows a lower applied signal strength, reducing false alarms. There are many combinations of high permeability, low coercivity, and low field strength acceptable for a given application.

In this way, the sterilization monitor acts as a marker for an object which may or may not have been properly exposed to sterilization conditions. In the case of an autoclave in a hospital, for example, if the monitor is placed next to the object and within the gauze wrapping, the sterilization of the object can be remotely monitored by passing the wrapped object through the interrogation zone 72 and detecting the harmonics for which the detection means 76 is tuned.

As summarized above, a monitor containing a low coercive force, high permeability material may be deactivated by changing the shape of the material so as to alter the demagnetization factor, and alternatively, may be deactivated by magnetically biasing the material with an external field. If the intensity of such a bias field is greater than the alternating fields applied by the detection system, the reversal of the magnetization of the material will be prevented altogether. If the bias field is less intense than the interrogation field, reversal may occur, but significantly less intense high order harmonics are produced. In any event, the response will be measurably altered.

As is known in the art, magnetized materials in close proximity to magnetic materials "bias" the magnetic materials, and thereby either prevent alternation of magnetization when in applied fields, or at least modify the response produced upon alternation. It is also known that materials with multiple magnetic pole patterns, i.e., multiple alternating north and south magnetic poles, exert a stronger bias.

A second embodiment, utilizing magnetic bias effects, where the bias field is provided by a second, permanently magnetized element, is shown in FIG. 3. The monitor comprises a housing 30 within which are positioned a high permeability, low coercive force magnetic material 34, a magnetized material 36, and a temperature/steam sensitive material 38. The housing 30 must be comprised of a material which will withstand the elevated temperatures, humidity levels, and other conditions present in sterilization equipment such as autoclaves. In the preferred embodiment, the housing 30 is comprised of 0.030 inch (0.76 millimeter) thick polypropylene, assembled by means known in the art for producing an assembly which will withstand the same conditions as the housing. Another suitable material for the housing is heavy-duty cardboard, or "poster board." The housing is box-shaped with rectangular sides and a rectangular top cover 35.

The steam window 32, suitably adhered to the top cover 35, comprises a material which will pass saturated steam into the monitor. Preferably this is 0.002 inch (0.05 millimeters) thick polypropylene. The total area of the passages 33 through which steam passes is chosen to allow sufficient quantities of steam to reach the temperature/steam sensitive material 38. In the preferred embodiment shown in FIGS. 3 and 4, two passages 33 are shown, one located on each side of the central portion of the top cover 35 which lies directly above the temperature/steam sensitive material 38.

The magnetized material 36 is held in position by a tablet-shaped amount of temperature/steam sensitive material 38, which is located between the upper portion of the housing and the magnetized material. The magnetic material 34 is inhibited from producing a detectable response when the magnetized material 36 is in close proximity to the magnetic material 34. The height of the tablet is chosen to force the magnetized material 36 against the magnetic material 34. This increases the biasing of the magnetic material 34 by the magnetized material 36. The housing 30 is constructed so as to subject the magnetized material 36 to spring tension which would tend to separate it from the magnetic material 34 if the tablet were removed, thereby decreasing the bias effect on magnetic material 34. In the embodiment shown, the housing 30 is constructed to provide for grooves 31 in which the ends of the magnetized material 36 are located, thereby suspending the magnetized material 36 above the magnetic material 34. The grooves 31 also fix the end portion of the magnetized material 36, thereby allowing the magnetized material to bend beneath the tablet-shaped temperature/steam sensitive material 38.

In the preferred embodiment, the magnetized material 36 is a cylindrical wire of stainless steel with a multiple magnetic pole pattern. Because the magnetic material 34 does not move in this embodiment, it need not be amorphous, but amorphous materials are still preferred.

Upon exposure to sterilization conditions, the steam passes through steam window 32 and thence passages 33 to temperature/steam sensitive material 38 which melts, releasing magnetized material 36 to move away due to spring tension from magnetic material 34, decreasing the bias effect of magnetized material 36 on allows magnetic material 34 and thereby allowing magnetic material 34 to generate a detectable response upon interrogation by suitable external fields. It has been found that separations as small as 0.05 inch (0.127 centimeters) are sufficient to allow the detectable response.

An example of a sterilization monitor, denoted M1, was constructed following the design shown in FIGS. 3 and 4. The housing was assembled with multiple layers of Artist's Poster Board, available from the Crescent Company, each layer approximately 0.05 inch (1.27 millimeters) thick. The layers were held together with 0.002 inch (0.05 millimeter) thick type 467 transfer adhesive, available from the Minnesota Mining and Manufacturing Company. The assembled monitor was 3 inches (7.62 centimeters) long, 0.75 inch (1.9 centimeter) wide, and 0.375 inch (0.95 centimeter) thick. The magnetic material 34 was a strip of amorphous foil, composed of cobalt (68.5 atomic percent) boron (12.4%), silicon (10%), iron (4.2%), nickel (3.4%), and molybdenum (1.5%). This material is available from Allied-Signal Corporation as type 2705M. The strip of amorphous foil was 3 inches (7.62 centimeters) long, 0.0625 inch (0.16 centimeter) wide, and 0.008 (0.2 millimeter) inch thick. The magnetized material 36 was type 302 stainless steel wire, 3 inches (7.62 centimeters) long and 0.02 inch (0.5 centimeter) in diameter. The wire was magnetized with multiple alternating north and south poles, spaced approximately 0.15 inch (3.81 millimeter) apart. The meltable material was a 0.25 inch (0.635 centimeter) diameter tablet of 100% salicylamide.

The steam window 32 was 0.002 inch (0.05 millimeter) thick polypropylene. Each passage 33 was circular with a diameter of 0.219 inch (0.56 centimeters). This size of passage was tested to verify that the temperature/steam sensitive material would melt after no less than 1 minute but no more that 3 minutes exposure to 270° F. (132° C.) saturated steam. This cycle was chosen because a typical hospital autoclave cycle is a minimum of 3 minutes saturated steam exposure at 270° F. (132° C.).

Sterilization monitor M1 was exposed to an external interrogation field oscillating at 60 Hz, and having a peak intensity of 15 Oersteds at the field generator and 0.8 Oersteds at the location of the monitor. The detector was tuned to detect the fourth through seventh harmonics of the applied signal. The monitor did not generate a detectable response upon interrogation.

The sterilization monitor was then exposed to elevated temperature and saturated steam in a Biological Indicator Evaluation Resistometer (BIER) vessel, manufactured by the Joslyn Valve Company. This is a device used in the art for simulating the conditions within commercial autoclaves. It provides the same temperature/steam cycles as commercial equipment without the "warm-up" cycle common in commercial equipment. (The warm-up cycle is not involved in the sterilization cycle.) The sterilization monitor was exposed to three minutes of 270° F. (132° C.) steam.

The monitor was again exposed to the interrogation field, and it did generate a detectable response. This verified that this specific embodiment successfully detected sterilization conditions.

FIGS. 5 and 6 show a third embodiment of the invention, in which a magnetized material is also used to bias a field-responsive material. As before, the housing 50 must be comprised of a material which will withstand the elevated temperatures, humidity levels, and other conditions present in sterilization equipment such as autoclaves. In the preferred embodiment, the housing comprises a sheet of 0.005 inch (0.13 millimeter) thick aluminum, into which a semicircular groove or similar deformation is formed. A cover 52 is adhered to the housing. In the preferred embodiment, the cover comprises common adhesive masking tape. The cover material and adhesive must withstand the same conditions as the housing.

The magnetic material 54, magnetized material 56, and temperature/steam sensitive material 58 are located underneath the cover 52. Because the magnetic material 54 does not move in this embodiment, it need not be amorphous.

The magnetized material 56 is a multiplicity of particles substantially uniformly dispersed in a temperature/steam sensitive material 58. Iron oxide ($Fe_2O_3$) powder is preferred for the magnetized material 56.

The steam window 51, located between the housing 50 and cover 52, comprises a material which will pass saturated steam into the monitor. Preferably this is 0.002 inch thick polypropylene. The area of the window is chosen to allow sufficient quantities of steam to reach the temperature/steam sensitive material 58. This area is exposed to the sterilization process by means of an opening cut in the cover 52.

Once the monitor is constructed as shown, an external magnetic field having alternating poles is applied to magnetize the individual particles of magnetized material 56. The total external magnetic field produced by the magnetized particles 56 thereafter inhibits the response of the magnetic material 54.

After exposure to sterilization conditons at pressures above ambient pressure, followed by a return to atmospheric pressure, during which the steam passes through steam window 51 to contact temperature/steam sensitive material 58, the temperature/steam sensitive material 58 melts, and thus the uniformly displaced particles of magnetized material 56 are allowed to move. This sufficiently changes the total external force due to the individual fields of the magnetized particles 56 to charge the inhibition of the response of the magnetic material 34, and to allow the magnetic material 54 to generate a detectable response upon interrogation by suitable external fields.

The monitor is capped at each end with end pieces 60, which are preferably made of the same material as the housing 50 or cover 52.

A second example sterilization monitor M2 was constructed in the embodiment of FIGS. 5 and 6. The magnetic material 54 was a strip of amorphous foil, composed of cobalt (68.5 percent atomic weight), boron (12.4%), silicon (10%), iron (4.2%), nickel (3.4%), and molybdenum (1.5%). This material is available from Allied-Signal Corporation as type 2705M. The strip of amorphous foil was 2.625 inches (6.67 centimeters) long, 0.0625 inch (0.16 centimeter) wide, and 0.0008 inch (0.02 millimeter) thick. The magnetized material 56 was type 2300 iron oxide powder available from the Phizer Company. The meltable material was powdered salicylamide. The proportion was 15% iron oxide and 85% salicylamide by weight.

The steam window 52 was polypropylene, 0.25 inch (6.4 millimeter) in length, 0.125 inch (3.2 millimeter) in width, and 0.002 inch (0.05 millimeter) thick. This size was tested to determine if it could be used with one typical hospital autoclave cycle, which is a minimum of 3 minutes saturated steam exposure at 270° F. (132° C.).

The sterilization monitor M2 was exposed to an external interrogation field oscillating at 60 Hz, and having a peak intensity of 15 Oersteds at the field generator and 0.8 Oersteds at the location of the monitor. The detector was tuned to detect the fourth through seventh harmonics of the applied signal. The monitor generated a detectable response upon interrogation. Then the monitor was exposed to an external magnetic field greater than 500 Oersteds. Again the interrogation field was applied, and now M2 exhibited no detectable response.

The sterilization monitor was then exposed to five minutes of 270° F. (132° C.) elevated temperature and saturated steam in an autoclave using a gravity cycle.

The monitor was again exposed to the interrogation field, and now the monitor generated a detectable response again. The magnitude of the second response was 89% normalized against the magnitude of the first response. This verified that this embodiment successfully detected conditions indicative of sterilization.

Although the invention has been described in embodiments suitable for hospital operations employing steam-dependent sterilization equipment, it will be readily seen by those skilled in the art that the invention may be adapted to other situations requiring a remote, non-visually verified temperature and/or chemical environment monitor. Such applications could include the use of other sterilization cycles (such as those employing elevated temperature only), or other types of sterilization equipment (such as ethylene oxide sterilizers), or non-sterilization applications (such as a storage temperature monitor for units of whole blood), etc. Such applications would not depart from the scope of the invention as defined by the following claims.

We claim:

1. A remote temperature monitor selectively interrogatable by a low intensity magnetic field comprising:
   means in the monitor for creating a remotely detectable magnetic response, comprising a magnetic material of high permeability and low coercivity, said creating means having at least two distinct magnetic states or configurations, a first state or configuration in which a first remotely detectable magnetic response is created upon a first interrogation, and a second state or configuration in which a second remotely detectable magnetic response which is different from the first state or configuration is created upon a second interrogation, and
   means in the monitor comprising a material which melts upon being heated to a predetermined temperature for changing said creating means from said first to said second state or configuration upon melting.

2. A monitor according to claim 1, wherein the first state comprises a spiral-like shape and the second state comprises a non-spiral-like shape, wherein said changing means comprises means for restricting said magnetic material in said first state prior to exposure to said predetermined temperature, and wherein the magnetic material possesses sufficient spring tension to move from the first state to the second state upon said exposure such that the magnetic material is no longer restricted.

3. A monitor according to claim 2, wherein said restricting means comprises means for encasing said magnetic material within said meltable material while the magnetic material is in the first state.

4. A monitor according to claim 1, wherein said magnetic material comprises an amorphous metal.

5. A monitor according to claim 1, wherein said changing means further comprises means for changing said first state upon exposure to a predetermined amount of steam.

6. A monitor according to claim 5, wherein said state changing means comprises a compound selected from the group consisting of 2-chloroacetamide, 2-ethoxybenzamide, benzoic acid, diphenyl succinate, dichlorophenol, dimethyl phenol, benzamide, urea, 1,4 dihydroxybenzophenone, hydroquinone, dioxime, ethylene ester of toluene sulfonic acid, salicylamide, salicylic acid, and 1,8-octane dicarboxylic acid.

7. A monitor according to claim 1, wherein said changing means further comprises a magnetized material magnetically coupled to maintain said creating means in said first state or configuration, and wherein said changing means comprises means for altering said magnetic coupling such that the creating means is changed to the second state or configuration.

8. A monitor according to claim 7, wherein said magnetic material comprises an amorphous metal.

9. A monitor according to claim 7 wherein said changing means further comprises means for changing said first state or configuration upon exposure to a predetermined amount of steam.

10. A monitor according to claim 9, wherein said changing means comprises a compound selected from the group consisting of 2-chloroacetamide, 2-ethoxybenzamide, benzoic acid, diphenyl succinate, dichlorophenol, dimethyl phenol, benzamide, urea, 1,4 dihydroxybenzophenone, hydroquinone, dioxime, ethylene ester of toluene sulfonic acid, salicylamide, salicylic acid, and 1,8-octane dicarboxylic acid.

11. A monitor according to claim 10, wherein said changing means comprises means for restricting said magnetized material in said first configuration prior to exposure to said predetermined temperature, and wherein the magnetized material possesses sufficient spring tension to move from the first configuration to the second configuration upon said exposure.

12. A monitor according to claim 7, wherein said magnetized material comprises particles substantially uniformly dispersed in said meltable material, thereby creating an extended magnetic field to maintain said first response.

13. A monitor according to claim 12, wherein said magnetic material comprises an amorphous metal.

14. A monitor according to claim 13, wherein said changing means further comprises means for changing said first state upon exposure to a predetermined amount of steam.

15. A monitor according to claim 14, wherein said changing means comprises a compound selected from the group consisting of 2-chloroacetamide, 2-ethoxybenzamide, benzoic acid, diphenyl succinate, dichlotophenol, dimethyl phenol, benzamide, urea, 1,4 dihydroxybenzophenone, hydroquinone, dioxime, ethylene ester of toulene sulfonic acid, salicylic acid, salicylamide, and 1,8-octane dicarboxylic acid.

* * * * *

UNITED STATES PATENT AND TRADEMARK OFFICE
CERTIFICATE OF CORRECTION

PATENT NO. : 4,850,716

DATED : July 25, 1989

INVENTOR(S) : Dennis L. Baker, Steven S. Kirckof, Dan J. Morse and Chester Piotrowski It is certified that error appears in the above-identified patent and that said Letters Patent is hereby corrected as shown below:

Col. 3, line 45, after "the" and before "cylinder" insert -- area of the material (and hence the diameter of the --.

Signed and Sealed this

Thirty-first Day of July, 1990

Attest:

HARRY F. MANBECK, JR.

Attesting Officer     Commissioner of Patents and Trademarks